United States Patent [19]

McClure et al.

[11] Patent Number: 5,549,652
[45] Date of Patent: Aug. 27, 1996

[54] CARDIAC WALL MOTION-BASED AUTOMATIC CAPTURE VERIFICATION SYSTEM AND METHOD

[75] Inventors: Kelly H. McClure, Simi Valley; Sheldon B. Moberg, Kagel Canyon, both of Calif.

[73] Assignee: Pacesetter, Inc., Sylmar, Calif.

[21] Appl. No.: 152,659

[22] Filed: Nov. 15, 1993

[51] Int. Cl.$^6$ ..................................................... A61N 1/37
[52] U.S. Cl. .................................................. 607/28; 607/7
[58] Field of Search .................................. 607/5, 6, 7, 8, 607/28, 27, 11

[56] References Cited

U.S. PATENT DOCUMENTS

| | | |
|---|---|---|
| 3,757,790 | 9/1973 | Herrmann . |
| 3,757,792 | 9/1973 | Mulier et al. . |
| 3,777,762 | 12/1973 | Nielsen . |
| 3,800,801 | 4/1974 | Gaillard . |
| 3,815,611 | 6/1974 | Denniston, III . |
| 4,091,817 | 5/1978 | Thaler . |
| 4,140,132 | 2/1979 | Dahl . |
| 4,232,679 | 11/1980 | Schulman . |
| 4,305,396 | 12/1981 | Wittkampf et al. . |
| 4,428,378 | 1/1984 | Anderson et al. . |
| 4,485,813 | 12/1984 | Anderson et al. .............. 128/675 |
| 4,674,508 | 6/1987 | DeCote . |
| 4,686,988 | 8/1987 | Sholder . |
| 4,708,143 | 11/1987 | Schroeppel . |
| 4,774,950 | 10/1988 | Cohen . |
| 4,790,317 | 12/1988 | Davies . |
| 4,827,936 | 5/1989 | Pless et al. . |
| 4,895,152 | 1/1990 | Callaghan et al. .............. 607/28 |
| 4,967,748 | 11/1990 | Cohen . |
| 4,969,464 | 11/1990 | Callaghan et al. .............. 607/28 |
| 4,989,602 | 2/1991 | Sholder et al. . |
| 5,014,700 | 5/1991 | Alt . |
| 5,031,615 | 7/1991 | Alt . |
| 5,040,534 | 8/1991 | Mann et al. . |
| 5,040,535 | 8/1991 | Mann et al. . |
| 5,044,366 | 9/1991 | Alt . |
| 5,144,948 | 9/1992 | Andersson et al. . |
| 5,320,643 | 6/1994 | Roline et al. .............. 607/28 |
| B1 4,232,679 | 5/1988 | Schulman . |

FOREIGN PATENT DOCUMENTS 572799   12/1993   European Pat. Off. ................. 607/28

OTHER PUBLICATIONS

Atochem Sensors, Inc. Product Brochure, *Standard and Custom Piezo Film Components*, pp. 1–10 (1991).
Bacharach, David W. et al., "Activity–Base Pacing: Comparison of a Device Using an Accelerometer Versus a Piezoelectric Crystal," *PACE*, vol. 15, pp. 188–196 (Feb. 1992).
Piezo Electric Products, Inc., "Piezoceramic Design Notes," *SENSORS* (Mar. 1984).
Salerno, David M. et al., "Seismocardiography: A New Technique for Recording Cardiac Vibrations. Concept, Method, and Initial Observations," *Journal of Cardiovascular Technology*, vol. 9, No. 2, 1990, pp. 111–118.

(List continued on next page.)

*Primary Examiner*—William E. Kamm
*Assistant Examiner*—Scott M. Getzow
*Attorney, Agent, or Firm*—Lisa P. Weinberg

[57] ABSTRACT

An improved implantable cardiac stimulating device that performs cardiac wall motion-based automatic capture verification system is provided. Pacing pulses of varying energy content are administered to a patient's heart, and the response of the patient's heart is sensed by a cardiac wall motion sensor. The cardiac wall motion sensor provides a signal which is analyzed to determine the patient's capture threshold, defined as the minimum amount of electrical stimulation required to evoke a cardiac contraction. The device then sets the amount of electrical stimulation at a level safely above the measured capture threshold. Capture verification may be performed at predetermined time intervals, on demand, or upon the occurrence of a significant cardiac event. Capture verification can also be performed on every pacing pulse delivered by the implantable cardiac stimulating device.

48 Claims, 3 Drawing Sheets

OTHER PUBLICATIONS

Salerno, David M. et al., "Seismocardiography for Monitoring Changes in Left Ventricular Function During Ischemia," *Chest,* vol. 100, pp. 991–993 (Oct. 1991).

Salerno, David M. et al., "Seismocardiographic Changes Associated With Obstruction of Coronary Blood Flow During Balloon Angioplasty," *The American Journal of Cardiology,* vol. 68, pp. 201–207 (Jul. 15, 1991).

Sandler, H. et al., "Miniature Implantable Accelerometers," pp. 165–174.

Ovsyshcher et al., "First Derivative of Right Ventricular Pressure, dP/dt, as a Sensor for a Rate Adaptive VVI Pacemaker: Initial Experience," *PACE,* vol. 15, pp. 211–218 (Feb. 1992).

CARDIAC WALL MOTION-BASED AUTOMATIC CAPTURE VERIFICATION SYSTEM AND METHOD

FIELD OF THE INVENTION

This invention relates generally to implantable cardiac stimulating devices, and particularly to implantable stimulating devices that include systems for automatically determining the amount of electrical stimulation that is required to induce a cardiac contraction in a patient. More particularly, this invention is directed toward an automatic capture verification system and method that uses cardiac wall motion to determine when a pacing pulse has effectively stimulated a patient's heart.

BACKGROUND OF THE INVENTION

A pacemaker is an implantable medical device which delivers electrical stimulation pulses to cardiac tissue to relieve symptoms associated with bradycardia—a condition in which a patient cannot maintain a physiologically acceptable heart rate. Early pacemakers delivered stimulation pulses at regular intervals in order to maintain a predetermined heart rate, which was typically set at a rate deemed to be appropriate for the patient at rest. The predetermined rate was usually set at the time the pacemaker was implanted, and in more advanced devices, could be set remotely by a medical practitioner after implantation.

Early advances in pacemaker technology included the ability to sense intrinsic cardiac activity (i.e., the intracardiac electrogram, or "IEGM"). This led to the development of "demand pacemakers," so named because they deliver stimulation pulses only as needed by the heart. Demand pacemakers are capable of detecting a spontaneous cardiac contraction which occurs within a predetermined time period (commonly referred to as the "escape interval") following a preceding contraction (whether spontaneous or evoked). When a naturally occurring contraction is detected within the escape interval, a demand pacemaker does not deliver a pacing pulse.

Pacemakers such as those described above proved to be extremely beneficial in that they successfully reduced or eliminated seriously debilitating and potentially lethal effects of bradycardia in many patients. However, since pacemakers are implantable devices, a surgical procedure is required when pacing therapy is deemed appropriate by a medical practitioner. Further, many patients who receive pacemakers must expect to undergo several surgical procedures, because pacemakers have a limited life span, and therefore require replacement from time to time. Of course, it is always desirable to minimize the number of surgical procedures that must be performed on a patient to improve safety and reduce costs.

The life span of most pacemakers is dictated by the rate at which their batteries drain. Thus, a substantial effort has been directed toward minimizing the amount of energy used by pacemakers, while ensuring that the devices continue to deliver effective therapy. Demand pacemakers (discussed above) effectively reduce battery drain by delivering pacing pulses only when required. However, each pacing pulse delivered by a demand pacemaker may have a significantly higher energy content than that required to induce a cardiac contraction. Thus, even after the development of demand pacemakers, there remained an opportunity for further improvements in the area of pacemaker energy utilization.

The minimum amount of electrical stimulation that effectively evokes a cardiac contraction is commonly referred to as a patient's "capture threshold." Unfortunately, capture threshold varies significantly among patients; therefore, the amount of electrical stimulation provided by a pacemaker cannot be permanently set by the manufacturer. Rather, stimulus parameters must be individually set for each patient immediately after implantation and during subsequent office visits.

Determining a particular patient's capture threshold is a relatively simple procedure when performed during an office visit. Essentially, the medical practitioner can remotely adjust the amount of electrical stimulation downward from a maximum value that is known to elicit a contraction for all patients. Once the amount of electrical stimulation falls below the patient's capture threshold, a heart beat is not detected, and the medical practitioner then upwardly adjusts the amount of electrical stimulation beyond the last successful level.

Typically, a substantial safety margin is added to the measured capture threshold to ensure that the pacemaker continues to evoke contractions over an extended period of time. The safety margin is necessary because a patient's capture threshold varies over time—sometimes dramatically during the first few months following implantation. However, by adding such a large safety margin, it is almost assured that the pacemaker will be wasting significant amounts of energy during its life span.

In an effort to reduce the amount of energy wasted, pacemakers have been developed which automatically evaluate the patient's capture threshold during normal operation. These devices are also capable of automatically adjusting the amount of electrical stimulation in response to changes to the capture threshold. These features (which in combination are commonly referred to as "autocapture"), significantly reduce battery drain, because higher energy pacing pulses are delivered only when needed by the patient. Although most of these devices continue to add a safety margin to the measured capture threshold, the safety margin can be greatly reduced, especially when the capture threshold is measured frequently.

Prior art pacemakers which perform autocapture commonly use the patient's IEGM to determine when a pacing pulse has evoked a cardiac contraction. These prior art pacemakers sample the IEGM immediately after a pacing pulse is delivered. The shape of the IEGM waveform indicates whether the pacing pulse successfully captured the heart. If an evoked R-wave is detected in the IEGM soon after the pacing pulse, then capture is confirmed, and the pacemaker may then reduce the amount of electrical stimulation. If an evoked R-wave is not detected, then the pacemaker has reduced the amount of electrical stimulation too much. When this occurs, the pacemaker sets the amount of electrical stimulation back to the previous level that successfully evoked a contraction, and adds a safety margin.

Pacemakers that perform IEGM-based autocapture present several drawbacks, particularly relating to signal processing, which have proven difficult to overcome. For example, it is extremely difficult to accurately sense the IEGM immediately after a pacing pulse is delivered, due to the presence of residual electrical effects in the immediate vicinity of the pacing electrodes. These residual effects (commonly known as "afterpotentials") interfere with the pacemaker's ability to sense the IEGM. Indeed, most pacemakers enter a refractory period immediately after a pacing pulse is delivered, during which time the sensing circuitry is deactivated, for the specific purpose of avoiding undesirable sensing of afterpotentials.

Pacemakers which perform IEGM-based autocapture must therefore make certain accommodations to overcome the difficulties described above. For example, U.S. Pat. No. 3,757,792 describes a pacemaker which provides an IEGM-based autocapture feature, but which employs separate pacing and sensing leads. Interference from afterpotentials may be avoided if the sensing lead if it is placed sufficiently far from the pacing lead. However, the use of additional leads is undesirable, because it adds cost to the pacing system and complexity to the surgical procedure during which the pacemaker is implanted. In addition, the use of separate leads may limit the options available to the medical practitioner in configuring the system to meet the needs of a particular patient (e.g., lead selection, lead location, etc.).

If separate leads are not used, then highly specialized sensing circuitry is typically used to discern the IEGM over the afterpotentials. This approach is also undesirable, because the additional circuitry required to distinguish the IEGM from the afterpotentials may draw more current than would otherwise be the case, which offsets some of the energy savings achieved through implementing autocapture.

What is needed, therefore, is an improved pacemaker that automatically sets the amount of electrical stimulation provided by pacing pulses in accordance with a patient's capture threshold, without relying on the patient's IEGM. The improved pacemaker should perform autocapture without using leads that otherwise would not be necessary, and should not require processing circuitry that significantly increases battery drain.

SUMMARY OF THE INVENTION

The disadvantages and limitations of the previously known pacemakers that perform autocapture as described above are overcome by the present invention. With this invention, a cardiac wall motion-based automatic capture verification system is provided. The present invention allows an implantable cardiac stimulating device which provides bradycardia pacing therapy to automatically adjust pacing pulse parameters so that the amount of electrical stimulation can be greatly reduced without compromising safety.

Many of the advantages of the present invention stem from the use of a signal representative of cardiac wall motion, instead of the patient's IEGM, to determine the patient's capture threshold. The cardiac wall motion signals used in accordance with the present invention are not susceptible to interference from pulse-induced afterpotentials. Thus, the use of separate sensing leads and specialized IEGM processing circuitry can be advantageously avoided.

In some respects, the cardiac wall motion-based automatic capture verification system of the present invention and prior art IEGM-based systems perform similarly. The system of the present invention delivers pacing pulses to the patient's heart, starting at a maximum amount of electrical stimulation that is known to evoke a cardiac contraction in all patients, and gradually reduces the amount of electrical stimulation provided by successive pacing pulses. In one embodiment, the amount of electrical stimulation is reduced by reducing the stimulus amplitude (i.e., the pulse voltage); however, similar principles may be applied using other pacing parameters, such as pulse width. In addition, the principles of the present invention may be applied equally to constant voltage and constant current devices.

As the amount of electrical stimulation is gradually reduced, the system determines if the pacing pulses are eliciting contractions by monitoring a signal provided by a cardiac wall motion sensor instead of the IEGM. For as long as the amount of electrical stimulation is greater than the patient's capture threshold, cardiac contractions are detected, and the system continues to reduce the amount of electrical stimulation. At some point in the process, the amount of electrical stimulation falls below the patient's capture threshold, and thus fails to evoke a contraction. The system receives a signal from the cardiac wall motion sensor indicative of the failure of the heart to contract, and in response, the amount of electrical stimulation is increased to the lowest level that previously evoked a cardiac contraction (which level is approximately equal to the patient's capture threshold). The system then checks to ensure that the previously successful amount of electrical stimulation still evokes a cardiac contraction. If it does not (perhaps due to a hysteresis effect), the amount of electrical stimulation is further increased until a contraction is detected by the cardiac wall motion sensor.

In the preferred embodiment of the present invention, a safety margin is added to the patient's measured capture threshold to ensure reliability. However, the safety margin can be significantly reduced, especially when the implantable cardiac stimulating device is programmed to perform capture verification frequently. Further, the preferred embodiment of the invention provides a continuous capture verification option, which allows for reduction of the safety margin to the lowest possible level. When this option is selected, the system performs cardiac wall motion-based automatic capture verification as described above a first time to determine the patient's capture threshold. The system then tests all pulses following the initial test procedure to determine if they evoke cardiac contractions. When a pacing pulse does not evoke a contraction, the system incrementally increases the amount of electrical stimulation until a contraction is evoked. This option provides a rapid response to sudden increases in the patient's capture threshold, thereby allowing for an even greater reduction of the safety margin.

As previously mentioned, many of the advantages of the present invention are derived from the use of a cardiac wall motion sensor, instead of the patient's IEGM, to measure the response of the patient's heart to varying electrical stimuli. The system is flexible, in that a variety of sensors that are capable of detecting cardiac contractions can be used, including pressure sensors, thermal dilution sensors, and accelerometers. Cardiac wall motion sensors that are particularly well-suited to be used in the present context are described in commonly assigned, copending U.S. patent application Ser. No. 08/091,636, filed Jul. 14, 1993, entitled "IMPLANTABLE LEADS INCORPORATING CARDIAC WALL MOTION SENSORS AND METHOD OF FABRICATION AND A SYSTEM AND METHOD FOR DETECTING CARDIAC ARRHYTHMIAS USING A CARDIAC WALL MOTION SENSOR SIGNAL," which is hereby incorporated by reference in its entirety. That patent application discloses a variety of implantable leads, including endocardial leads, myocardial active-fixation leads, and epicardial patch electrodes, which incorporate cardiac wall motion sensors that are responsive to cardiac wall accelerations. One advantage of using such leads is that the lead which contains the cardiac wall motion sensor may contain at least one (and perhaps both) of the electrodes that are used to deliver pacing pulses, thereby advantageously reducing the number of leads that need to be implanted in the patient's body.

The signal provided by the cardiac wall motion sensor used in accordance with the present invention can be filtered and processed using conventional techniques. The processed signal can be analyzed by a microprocessor, to determine when pacing pulses elicit cardiac contractions. Depending on the information present in the processed signal, the microprocessor adjusts the amount of electrical stimulation upwardly or downwardly, as described above.

The frequency at which the cardiac wall motion-based automatic capture verification system determines the patient's capture threshold may be changed from time to time as deemed appropriate by the medical practitioner. In addition, the medical practitioner may initiate capture verification during a follow-up visit. Further, the system may automatically perform capture verification upon the occurrence of certain cardiac events. For example, if the implantable cardiac stimulating device provides higher energy electrical stimulation therapies (e.g., cardioversion or defibrillation shocks) in addition to bradycardia pacing therapy, it may be desirable to re-evaluate the patient's capture threshold after higher energy therapies are administered.

In another aspect of the present invention, a method of providing cardiac wall motion-based automatic capture verification is provided. In addition, a convenient method for distinguishing ventricular fibrillation from cardiac asystole is provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE PREFERRED EMBODIMENT

Figure 1:
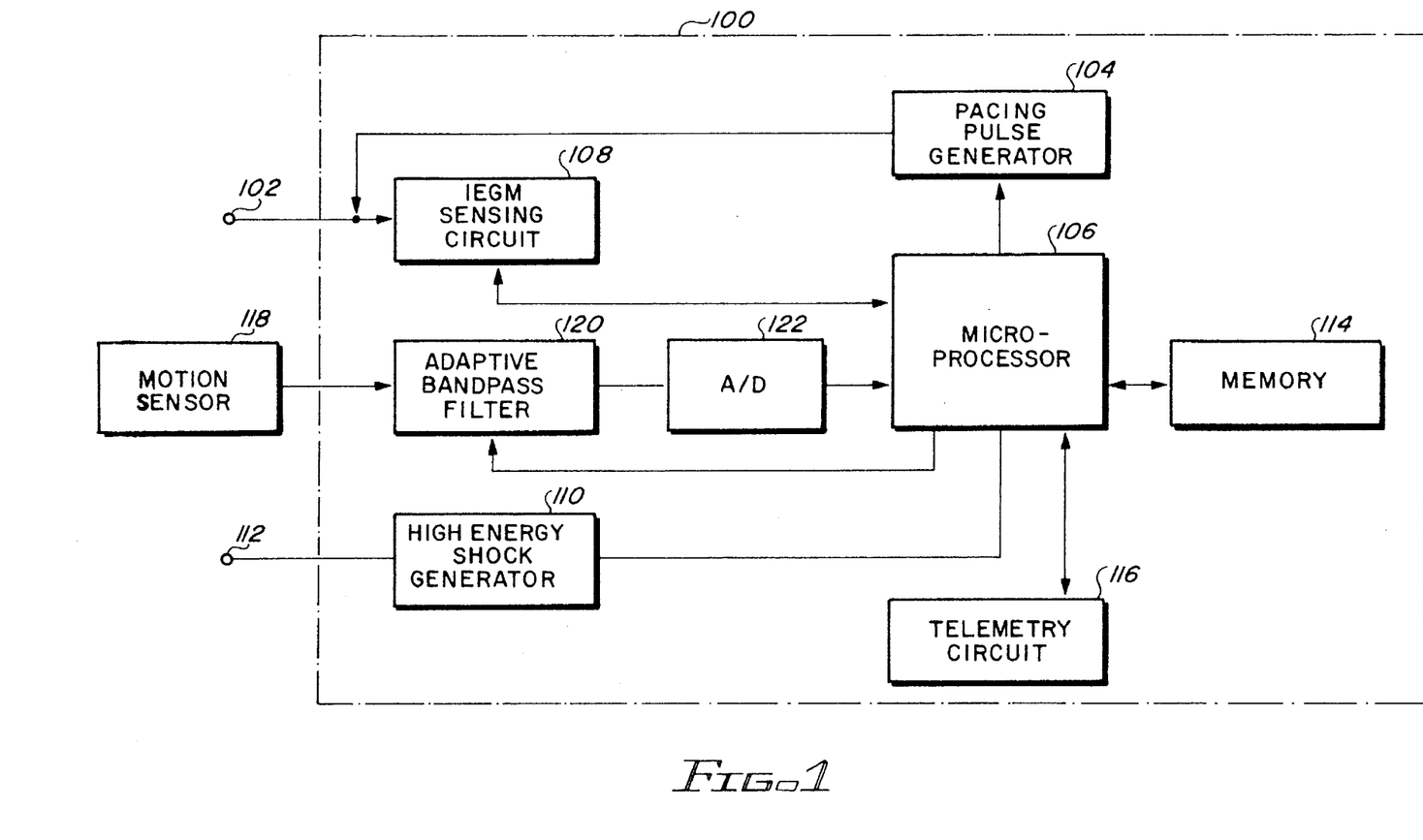
FIG. 1 is a block diagram of an implantable cardiac stimulating device that is capable of providing bradycardia pacing therapy and cardiac wall motion-based automatic capture verification in accordance with the principles of the present invention.

In FIG. 1, a block diagram is shown representing an implantable cardiac stimulating device 100 which performs cardiac wall motion-based automatic capture verification in accordance with the principles of the present invention. The implantable cardiac stimulating device 100, as described below, is capable of providing bradycardia pacing therapy as well as higher energy therapies, such as cardioversion and defibrillation shocks. However, cardiac wall motion-based automatic capture verification can be easily implemented in a simpler device, such as a dedicated bradycardia pacemaker, in view of the description below.

The implantable cardiac stimulating device 100 delivers therapeutic electrical stimulation to a patient's heart (not shown) through leads 102 and 112 which are attached at one end to the implantable cardiac stimulating device 100, and at the other end (not shown) to a selected region of cardiac tissue (not shown). In the embodiment shown in FIG. 1, at least one pacing lead 102 is used to deliver pacing pulses generated by a pacing pulse generator 104 (which may be conventional) in accordance with instructions provided by a microprocessor 106.

The implantable cardiac stimulating device 100 may operate as a demand pacemaker, in that the delivery of a pacing pulse provided by the pacing pulse generator 104 may be inhibited by a spontaneous cardiac contraction which occurs during the escape interval. Demand pacing is accomplished as follows. When pacing pulses are not being administered, the pacing lead 102 senses the patient's IEGM, which is communicated to an IEGM sensing circuit 108. The IEGM sensing circuit 108 provides a control signal to the microprocessor 106, indicative of whether a cardiac contraction has occurred. The microprocessor 106 determines if a sensed contraction occurred within the escape interval, and if so, it inhibits the pacing pulse generator 104 from generating a pacing pulse. Otherwise, pacing pulses continue to be administered.

For a brief period of time following the delivery of each pacing pulse, the implantable cardiac stimulating device 100 enters a refractory period. During the refractory period, the microprocessor 106 disables the IEGM sensing circuit 108, to avoid undesirable sensing of a pulse-induced after-potential. The duration of the refractory period usually extends beyond the time when a QRS complex would be expected following a pacing pulse. Thus, as explained above, IEGM-based autocapture systems must make special accommodations (e.g., separate sensing leads or specialized IEGM sensing circuitry) in order to discern over the pulse-induced afterpotential, a QRS complex indicative of an evoked contraction. As described below, the present invention overcomes this limitation.

The implantable cardiac stimulating device 100, as mentioned above, may be capable of providing higher energy shock therapies to interrupt more severe cardiac arrhythmias. For example, cardioversion shocks may be administered to revert ventricular tachycardia (VT), and defibrillation shocks may be administered to interrupt ventricular fibrillation (VF). These higher energy shocks are generated by a high energy shock generator 110 (which may be conventional), and are delivered to the patient's heart through at least one shocking lead 112. Although the pacing lead 102 and the shocking lead 112 are shown as physically separate leads, their respective electrodes may be provided by a single lead (not shown). Indeed, a great variety of lead configurations may be used in accordance with the principles of the present invention, so as to not diminish the flexibility that a medical practitioner normally has when selecting leads that meet the needs of a particular patient.

Like pacing therapy, higher energy shock therapies are administered under the control of the microprocessor 106. The microprocessor 106 receives a signal indicative of whether the patient is experiencing a severe arrhythmia (e.g., VT or VF) from the IEGM sensing circuit 108. If such an arrhythmia is detected, the microprocessor 106 causes the high energy shock generator 110 to generate a therapeutic shock of an appropriate energy content to revert the particular type of arrhythmia detected.

The manner by which the implantable cardiac stimulating device 100 delivers pacing therapy and higher energy shock therapies is controlled by the microprocessor 106 in accordance with parameters stored in a memory 114. Many of these parameters are known in the art (e.g., escape interval, refractory period, cardioversion shock energy, defibrillation shock energy, etc.), and they may be programmed by a medical practitioner using a programming unit (not shown) that communicates with the microprocessor 106 through a telemetry circuit 116. Certain other parameters, as described below, are used in connection with cardiac wall motion-based automatic capture verification.

As mentioned above, the limitations of prior art IEGM-based autocapture systems are overcome by the present invention. Many of the advantages of the present invention are achieved through the use of a cardiac wall motion sensor 118 which is responsive to contractile activity of the patient's heart. The cardiac wall motion sensor 118 provides a signal representative of cardiac wall motion to the implantable cardiac stimulating device 100, and the signal is processed to determine if a particular pacing pulse evoked a cardiac contraction.

In a preferred embodiment, the cardiac wall motion sensor 118 is mechanically coupled to the patient's heart by a lead that is also used to administer therapeutic electrical stimulation. For example, the cardiac wall motion sensor 118 may be disposed within or on the pacing lead 102 or the shocking lead 112. Using this approach, the number of leads that must be implanted in the patient's body is advantageously reduced.

A variety of sensors that are capable of detecting muscle contractions may be used as the cardiac wall motion sensor 118, including pressure sensors, thermal dilution sensors, and accelerometers. Sensors that are particularly well-suited for use in the present context are disclosed in the above-incorporated U.S. patent application Ser. No. 08/091,636, filed Jul. 14, 1993. That patent application discloses several types of implantable leads which incorporate accelerometer-based cardiac wall motion sensors. The accelerometer-based cardiac wall motion sensors provide signals which are indicative of cardiac mechanical activity including cardiac contractions following pacing pulses. In addition, the signals provided by the accelerometer-based cardiac wall motion sensors may be used by the microprocessor 106 as a substitute for, or in combination with, the patient's IEGM for detecting severe cardiac arrhythmias, as described in the above-incorporated patent application.

Signals from the cardiac wall motion sensor 118 are received by an adaptive bandpass filter 120 in the implantable cardiac stimulating device 100. During a calibration phase (described in detail below) the adaptive bandpass filter 120 is tuned by the microprocessor 106 to select relatively large amplitude, high slew rate signals that are associated with coherent cardiac contractions, and to reject signals caused by patient movements. The adaptive bandpass filter 120 may further process the signals using conventional techniques, such as averaging, integrating or double-integrating. The integral and double-integral of cardiac wall motion accelerations correspond to velocity and cardiac displacement. The filtered signals are then sampled and digitized by an analog-to-digital converter 122, and the resulting digital data indicative of cardiac contractile activity is provided to the microprocessor 106. The microprocessor 106 executes a program (the program code being stored in the memory 114) to perform cardiac wall motion-based automatic capture verification.

Figure 2:
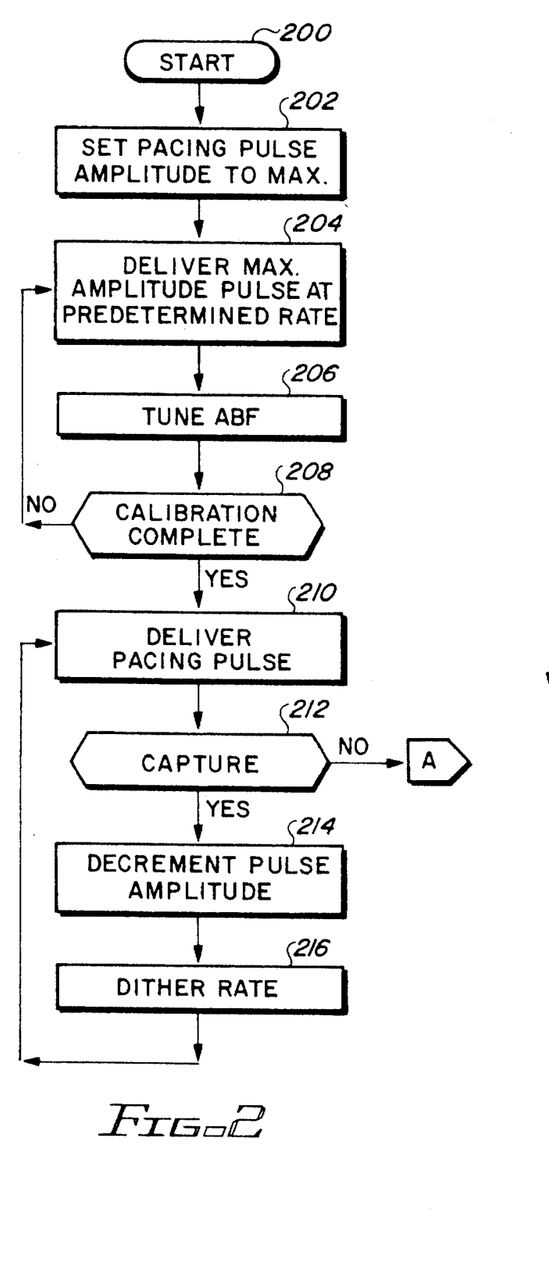
FIGS. 2 and 3 depict a logic flow diagram of a program executed by the microprocessor shown in FIG. 1, for controlling the cardiac wall motion-based automatic capture verification system of the present invention.
Figure 3:
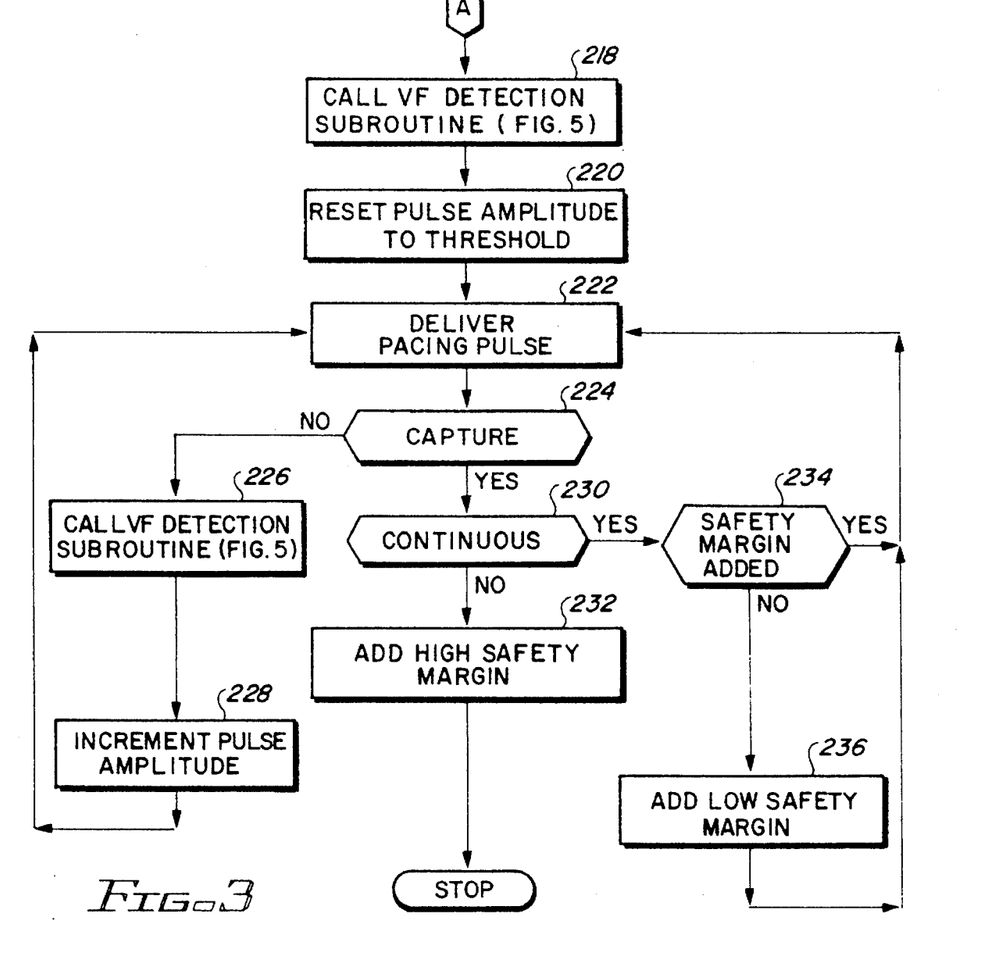

In FIGS. 2 and 3, a logic flow diagram representing a control program for the microprocessor 106 of FIG. 1, which may be implemented in suitable microcode or any high level language, is described. It should be understood that the control program diagrammed in FIGS. 2 and 3 pertains to cardiac wall motion-based automatic capture verification, and that the microprocessor 106 (FIG. 1) may perform many other control functions which are beyond the scope of the present invention.

In the preferred embodiment of the invention, there are three ways in which the control program of FIGS. 2 and 3 may be invoked. The first (and likely the most frequent) way is automatic execution at predetermined time intervals. Using an external programming unit (not shown), the medical practitioner can program the microprocessor 106 (FIG. 1) via the telemetry circuit 116 (FIG. 1) to store in the memory 114 (FIG. 1), an execution interval which is deemed to be appropriate for a particular patient. For example, during the first few months following implantation, the patient's capture threshold is likely to substantially increase. Therefore, frequently verifying the patient's capture threshold during this initial period (e.g., hourly) will ensure reliable performance of the implantable cardiac stimulating device 100 (FIG. 1), while avoiding the need to set the amount of electrical stimulation at the maximum level. After a follow-up visit, the medical practitioner can reprogram the execution interval so that capture verification is performed less frequently.

The second way in which the control program of FIGS. 2 and 3 may be invoked is on demand by the medical practitioner during an office visit. For some patients, the medical practitioner may prefer to be present when the amount of electrical stimulation is adjusted. Under these circumstances, periodic capture verification would be unnecessary. So instead, the medical practitioner can simply invoke the control program using an external programming unit (not shown) during an office visit, whenever it is desirable to perform capture verification.

The third way to invoke the control program of FIGS. 2 and 3 is applicable when the implantable cardiac stimulating device is capable of providing higher energy therapies (as is the case for the embodiment described with respect to FIG. 1). Specifically, certain events may trigger capture verification, such as the delivery of cardioversion or defibrillation shocks. This method of invoking the control program advantageously allows the implantable cardiac stimulating device 100 (FIG. 1) to accommodate changes to the patient's capture threshold which frequently occur after higher energy shocks are administered.

In the following discussion, automatic capture verification is described in terms of varying the pulse amplitude (e.g., the pulse voltage in a constant voltage device). However, it should be understood that similar principles may be applied to other pacing parameters such as pulse width, or pulse current in a constant current device.

The control program of FIGS. 2 and 3 begins at start 200, which is followed by a calibration sequence that includes steps 202, 204, and 206, and a test 208. At the step 202, the microprocessor 106 (FIG. 1) sets the pacing pulse generator 104 (FIG. 1) to generate stimulation pulses having a predetermined maximum amplitude (e.g., 5 volts). The predetermined maximum amplitude is stored as a parameter in the memory 114.

At the step 204, the microprocessor 106 (FIG. 1) causes the pacing pulse generator 104 (FIG. 1) to generate a stimulation pulse having the maximum amplitude, at a rate which is programmed to be faster than the patient's natural heart rate (e.g., 75 beats per minute). Both the number of pulses and the pulse rate may be stored as parameters in the memory 114 (FIG. 1). Since the rate is set to be faster than the patient's natural rhythm during the calibration phase, a contraction should be detected by the cardiac wall motion sensor 118 (FIG. 1) soon after the stimulation pulse is delivered. At the step 206, the microprocessor 106 (FIG. 1) tunes the adaptive bandpass filter 120 (FIG. 1) so that the digital signal provided by the analog-to-digital converter 122 (FIG. 1) is representative of cardiac contractions caused by the application of the maximum amplitude stimulation pulse, and not, for example, body motion. More precisely, the microprocessor 106 (FIG. 1) tunes the adaptive bandpass filter 120 (FIG. 1) so that an expected excursion appears in the signal provide by the cardiac wall motion sensor 118 (FIG. 1) within a predetermined period of time following each maximum amplitude pacing pulse delivered at the step 204.

At the test 208, the microprocessor 106 (FIG. 1) determines whether the calibration phase has been completed. Under most circumstances, sixty maximum amplitude stimulation pulses should be sufficient to properly calibrate the adaptive bandpass filter 120; however, this number can be stored as a parameter in the memory 114 (FIG. 1), and can be adjusted by the medical practitioner as needed. Until the calibration phase is completed, the program repeatedly loops back to the step 204, where the microprocessor 106 (FIG. 1) causes the pacing pulse generator 104 (FIG. 1) to generate another maximum amplitude pacing pulse.

Once the microprocessor 106 (FIG. 1) determines at the test 208 that the calibration phase has been completed, a step 210 is performed, at which the microprocessor 106 (FIG. 1) causes the pacing pulse generator 104 (FIG. 1) to generate a pacing pulse at the currently set amplitude. The first time the step 210 is performed, the pacing pulse amplitude will be the maximum amplitude set during the calibration phase.

Immediately after the pacing pulse is delivered at the step 210, the microprocessor 106 (FIG. 1) performs a test 212 to determine if the last pacing pulse evoked a cardiac contraction. The microprocessor 106 (FIG. 1) accomplishes this by analyzing the digital signal provided by the analog-to-digital converter 122 (FIG. 1) for a predetermined period of time following the delivery of the stimulation pulse.

If a digital signal representative of a cardiac contraction is received, the microprocessor 106 (FIG. 1) decrements the pacing pulse amplitude by a predetermined amount at a step 214. The amount by which the pacing pulse amplitude is decremented is stored as a parameter in the memory 114 (FIG. 1), and can be modified by the medical practitioner as desired. Decrementing the pacing pulse amplitude by about 0.1 volts should be satisfactory for most patients.

At the step 216, the microprocessor 106 (FIG. 1) slightly varies the timing of the delivery of pacing pulses, so that the rate at which the subsequent pulse is to be delivered is in fact different from the rate at which the previous pulse was delivered. This step (referred to as "dithering") reduces the possibility of the next pacing pulse being synchronized with a spontaneous depolarization. If such synchronization occurs, the spontaneous contraction will appear as an evoked contraction, thereby leading to a false determination of the patient's capture threshold. As explained below, the system provides another safeguard (in addition to dithering) to ensure that the implantable cardiac stimulating device 100 (FIG. 1) does not persistently deliver ineffective pacing pulses.

Following the step 216, the program loops back to the step 210, where the microprocessor 106 (FIG. 1) causes the pacing pulse generator 104 (FIG. 1) to generate a pacing pulse at the lower amplitude set at the step 214. A loop consisting of the test 212 and the steps 214, 216, and 210 is repeated until the microprocessor 106 (FIG. 1) determines at the test 212 that the most recent pacing pulse did not evoke a cardiac contraction.

Figure 4:
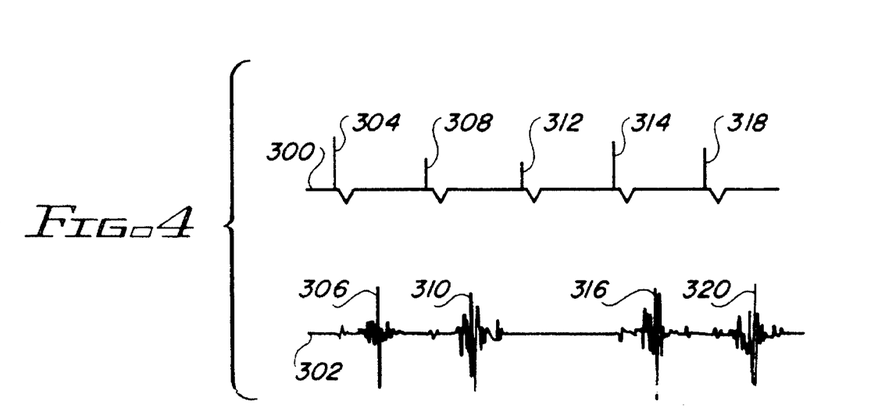
FIG. 4 depicts a waveform showing varying electrical stimulation pulses administered to a heart by the implantable cardiac stimulating device of FIG. 1 in accordance with the principles of the present invention, and a cardiac wall motion sensor signal showing the response of the heart to the varying electrical stimulation pulses.

The manner by which the microprocessor 106 (FIG. 1) evaluates the processed and digitized signal provided by the cardiac wall motion sensor 118 (FIG. 1) to adjust the pacing pulse amplitude may be fully appreciated by reference to the waveforms shown in FIG. 4. A waveform 300 depicts pacing pulses having amplitudes which are varied in accordance with the program steps described with respect to FIGS. 2 and 3. A cardiac wall motion sensor signal 302 shows the response of the patient's heart (not shown) to the varying stimuli. For example, a pacing pulse 304 administered the first time the step 210 (FIG. 2) is performed has the predetermined maximum amplitude. Accordingly, an excursion 306 indicative of an evoked cardiac contraction appears in the signal 302 soon after the pacing pulse 304 is delivered.

The excursion 306 is detected by microprocessor 106 (FIG. 1) at the test 212 (FIG. 2). The step 214 (FIG. 2) is then performed to decrement the amplitude of the next pacing pulse. A pacing pulse 308 having the lower amplitude is then administered at the step 210 (FIG. 2), and it also evokes a cardiac contraction, as indicated by an excursion 310 in the signal 302. (The effect of "dithering" is not apparent in the waveforms shown in FIG. 4.) Another pacing pulse 312 having yet a lower amplitude is then administered, but this time, the pulse amplitude is lower than the patient's capture threshold. Thus, no corresponding excursion indicating a cardiac contraction appears in the signal 302, and the absence of an excursion within a predetermined time period following the pacing pulse 312 is detected by the microprocessor 106 (FIG. 1) at the test 212 (FIG. 2).

Figure 5:
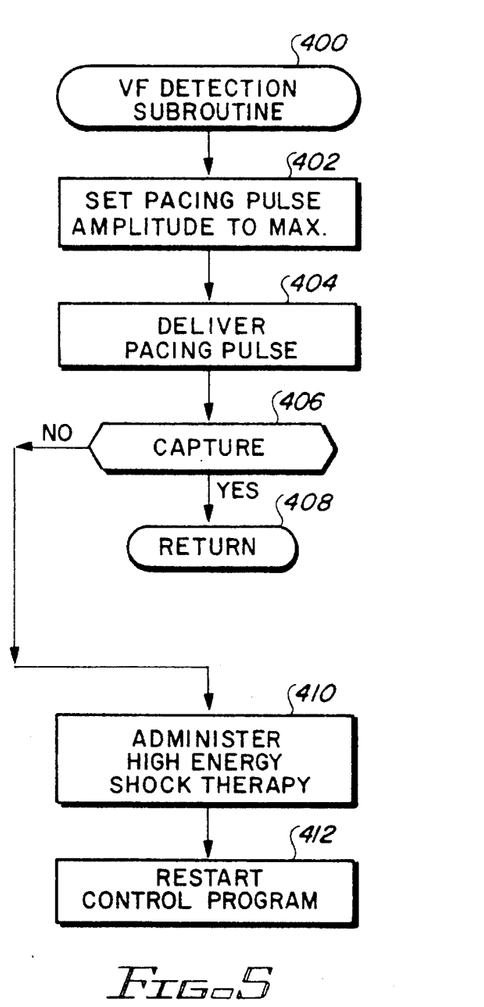
FIG. 5 is a logic flow diagram of a VF detection routine called by the program of FIGS. 2 and 3 in accordance with the principles of the present invention.

Referring briefly again to FIGS. 2 and 3, when a cardiac contraction is not detected at the test 212, a capture recovery sequence is performed to reset the pacing pulse amplitude to level that evokes a cardiac contraction. The first of the capture recovery steps is a step 218, at which a VF detection routine 400 (shown in FIG. 5) is called. Referring now to FIG. 5, the VF detection routine 400 advantageously serves two useful purposes. First, it prevents the implantable cardiac stimulating device 100 (FIG. 1) from repeatedly administering inappropriately low amplitude pacing pulses. Second, it provides a convenient method for distinguishing cardiac asystole from VF.

At a step 402, the microprocessor 106 (FIG. 1) once again sets the pacing pulse amplitude to the predetermined maximum value. The microprocessor 106 (FIG. 1) then causes the pacing pulse generator 104 (FIG. 1) to deliver a maximum amplitude pacing pulse. A test 406 is then performed to determine if the pacing pulse evoked a cardiac contraction. Except for extremely rare situations (described below), the maximum amplitude pacing pulse elicits a cardiac contraction, and control is then returned to the main program at a step 408.

Referring again to FIGS. 2 and 3, a step 220 is performed after control is returned from the VF detection routine 400 (FIG. 5). At the step 220, the microprocessor 106 (FIG. 1) resets the pacing pulse amplitude to the lowest level that previously evoked a cardiac contraction (i.e., the amplitude of the pacing pulse 308 of FIG. 4). Then at a step 222, the microprocessor 106 (FIG. 1) causes the pacing pulse generator 104 (FIG. 1) to generate a pacing pulse having the amplitude set at the step 220. Under most circumstances, this pulse should evoke a contraction; however, some patients experience a hysteresis effect which requires the pacing pulses that soon follow an ineffective pulse to have a higher amplitude than would otherwise be expected. To be sure this condition does not present a problem, a test 224 is performed, at which the microprocessor 106 (FIG. 1) determines if the pacing pulse was effective.

If it is determined at the test 224 that the pulse was not effective, then the VF detection routine 400 (FIG. 5) is again called at a step 226, which, as described above, serves to prevent repeated delivery of ineffective pacing pulses. Then, at a step 228, the microprocessor 106 (FIG. 1) sets the pacing pulse amplitude to be incrementally higher than the amplitude of the pacing pulse delivered at the last execution of the step 222. A loop consisting of the step 222, the test 224, the step 226, and the step 228 is repeated until the pacing pulse amplitude has been incremented to an extent sufficient to overcome the hysteresis effect. This safeguard also serves to correct an inappropriate determination of the patient's capture threshold resulting from synchronization of a pacing pulse with a spontaneous contraction at the step 210.

A successful execution of the capture recovery steps described above may be fully appreciated by further reference to the waveform 300 and the cardiac wall motion sensor signal 302 of FIG. 4. As previously explained, the pacing pulse 312 was determined at the test 212 (FIG. 2) to have an insufficient amplitude to evoke a cardiac contraction. The VF detection routine 400 (FIG. 5) is then executed at the step 218 (FIG. 3), thus causing a maximum amplitude pacing pulse 314 to be administered. The pacing pulse 314 successfully evokes a cardiac contraction, as indicated by an excursion 316 in the signal 302. The microprocessor 106 (FIG. 1) then sets the pulse amplitude at the lowest level that was previously successful at eliciting a cardiac contraction (i.e., the amplitude of the pacing pulse 308) at the step 220 (FIG. 3). The microprocessor 106 (FIG. 1) then, at the step 222 (FIG. 3), causes the pacing pulse generator 104 (FIG. 1) to deliver a pacing pulse 318 having the amplitude set at the step 220 (FIG. 3). An excursion 320 seen in the signal 302 indicates that the previously determined capture threshold remains valid.

Referring again to FIGS. 2 and 3, once capture is confirmed at the test 224, a test 230 is performed to determine if the medical practitioner has selected continuous capture verification. If continuous capture verification has not been selected, the microprocessor 106 (FIG. 1) adds a safety margin to the current pulse amplitude at a step 232, to ensure that the implantable cardiac stimulating device 100 (FIG. 1) reliably administers pacing therapy over an extended period of time. As explained below, the safety margin added at the step 232 is higher than the safety margin that needs to be added if continuous capture verification is being used. The pulse amplitude, including the safety margin, is maintained until the next time the control program of FIGS. 2 and 3 is invoked using any of the three methods described above. The control program then stops, and pacing therapy may then be administered in a manner that may otherwise be conventional.

Alternatively, at the test 230, it may be determined that the medical practitioner has opted to have the implantable cardiac stimulating device 100 (FIG. 1) perform continuous capture verification. This mode of operation advantageously allows the microprocessor 106 (FIG. 1) to test the effectiveness of every pacing pulse administered by the implantable cardiac stimulating device 100. Although this mode may drain energy reserves more quickly than less frequent capture verification, the savings achieved by reducing the safety margin may offset the loss. Further, continuous capture verification allows for rapid adjustments to the pacing amplitude if the patient's capture threshold suddenly changes, thus improving safety.

If continuous capture verification has been selected, the microprocessor 106 (FIG. 1) determines if a safety margin has already been added to a successful pulse amplitude at a test 234. If not (as would be the case the first time the test 234 is performed), the microprocessor 106 (FIG. 1) adds a safety margin to the current pulse amplitude at a step 236. However, since the effectiveness of every pacing pulse is tested in this mode, the safety margin can be significantly lower than that added at the step 232, when continuous capture verification has not been selected. The program then loops back to the step 222, at which the microprocessor 106 (FIG. 1) causes the pacing pulse generator 104 (FIG. 1) to deliver a pacing pulse having the amplitude set at the step 236.

The effectiveness of the pacing pulse delivered at the step 222 is evaluated at the test 224. If a cardiac contraction is not detected, the VF detection routine 400 (FIG. 5) is called at the step 226. However, when the VF detection routine 400 (FIG. 5) is called during continuous capture verification, additional consideration must be given to the possibility that a cause other than a change in the patient's capture threshold may be responsible for the absence of an expected cardiac contraction at the test 224. One possibility is that the patient may be experiencing VF.

When a patient experiences an episode of VF, the heart quivers chaotically, and the signal provided by the cardiac wall motion sensor 118 (FIG. 1) exhibits extremely low amplitude excursions. This signal may be difficult to distinguish from a signal representing cardiac asystole and therefore, the implantable cardiac stimulating device 100 (FIG. 1) may continue to deliver bradycardia pacing therapy instead of a more aggressive therapy, such as a defibrillation shock.

Referring again to FIG. 5, a convenient method for distinguishing VF from cardiac asystole is described. As explained above, the steps 402 and 404 serve to prevent a patient from having to withstand periods of ineffective pacing therapy while the patient's capture threshold is being determined. After the maximum amplitude pacing pulse is administered at the step 404, a cardiac contraction should be detected at the test 406.

If a cardiac contraction is not detected at the test 406, there is a strong possibility that the cardiac wall motion sensor signal being received by the microprocessor 106 (FIG. 1) is not representative of cardiac asystole, but rather VF. Under these circumstances, a step 410 is performed, at which the microprocessor 106 (FIG. 1) causes the high energy shock generator 110 (FIG. 1) to administer an appropriate form of therapy (e.g., a defibrillation shock) to revert the VF episode, in a manner that may otherwise be conventional. Then, at a step 412, the control program of FIGS. 2 and 3 is restarted (i.e., control is returned to the start 200). Restarting the control program is necessary, because the patient's capture threshold is likely to have significantly changed as a result of the administration of higher energy shock therapy.

If, however, it is determined at the test 406 that the pacing pulse delivered at the step 404 evoked a cardiac contraction, control is returned to the main program of FIGS. 2 and 3 at a point after the step 226. Referring again to FIGS. 2 and 3, a loop consisting of the step 226, the step 228, the step 222, and the test 224 is repeated until the pacing pulse amplitude has been incremented to an extent sufficient to elicit a cardiac contraction. Once capture is confirmed at the test 224, the program repeatedly executes another loop consisting of the test 230, the test 234, the step 222, and the test 224, until loss of capture is detected at the test 224. The step 236 is performed only once after each time the pacing pulse amplitude has been incremented.

Thus a cardiac wall motion-based automatic capture verification system is provided. One skilled in the art will appreciate that the present invention can be practiced by other than the described embodiments, which are presented for purposes of illustration and not of limitation, and the present invention is limited only by the claims which follow.

What is claimed is:

1. An implantable cardiac stimulating device for administering pacing pulses to cardiac tissue through an implantable stimulation lead, the device comprising:

a pacing pulse generator for generating the pacing pulses;

input circuitry for receiving a signal representative of cardiac wall motion; and control circuitry, coupled to the pacing pulse generator and the input circuitry, for regulating the pacing pulse generator and for evaluating the signal representative of cardiac wall motion to determine when the pacing pulses evoke cardiac contractions.

2. The implantable cardiac stimulating device of claim 1, wherein:

the signal representative of cardiac wall motion is a cardiac wall acceleration signal; and the input circuitry comprises means for receiving the cardiac wall acceleration signal.

3. The implantable cardiac stimulating device of claim 2, wherein the control circuitry further comprises:

means for detecting an excursion in the cardiac wall acceleration signal within a predetermined period of time following delivery of a selected pacing pulse, the excursion indicating that the selected pacing pulse evoked a cardiac contraction.

4. The implantable cardiac stimulating device of claim 1, wherein the control circuitry comprises:

means for adjusting an amount of electrical stimulation provided by the pacing pulses in response to an indication present in the signal representative of cardiac wall motion that a preceding pacing pulse did not evoke a cardiac contraction.

5. The implantable cardiac stimulating device of claim 4, wherein the control circuitry further comprises:

means for increasing the amount of electrical stimulation provided by the pacing pulses by a predetermined amount following every pacing pulse that does not evoke a cardiac contraction.

6. The implantable cardiac stimulating device of claim 1, wherein the control circuitry comprises:

means for determining a minimum amount of electrical stimulation that evokes a cardiac contraction.

7. The implantable cardiac stimulating device of claim 6, wherein the means for determining a minimum amount of electrical stimulation comprises:

means for decreasing an amount of electrical stimulation provided by the pacing pulses from a sufficient amount of electrical stimulation known to evoke a cardiac contraction until the signal representative of cardiac wall motion indicates a failure of a pacing pulse to evoke a cardiac contraction.

8. The implantable cardiac stimulating device of claim 7, wherein the means for decreasing the amount of electrical stimulation provided by the pacing pulses comprises:

means for decrementing the amount of electrical stimulation provided by the pacing pulses from the sufficient amount of electrical stimulation by a predetermined amount until the signal representative of cardiac wall motion indicates a failure of a pacing pulse to evoke a cardiac contraction.

9. The implantable cardiac stimulating device of claim 8, wherein the control circuitry further comprises:

means for resetting the amount of electrical stimulation provided by the pacing pulses to the minimum amount of electrical stimulation that evokes a cardiac contraction after the signal representative of cardiac wall motion indicates a failure of a pacing pulse to evoke a cardiac contraction.

10. The implantable cardiac stimulating device of claim 9, wherein the control circuitry further comprises:

means for adding a safety margin to the minimum amount of electrical stimulation.

11. The implantable cardiac stimulating device of claim 7, wherein the control circuitry further comprises:

means for dithering a rate at which the pacing pulses are delivered.

12. The implantable cardiac stimulating device of claim 6, wherein the control circuitry further comprises:

means for determining the minimum amount of electrical stimulation at predetermined time intervals.

13. The implantable cardiac stimulating device of claim 6, further comprising:

means for programming the minimum amount of electrical stimulation.

14. The implantable cardiac stimulating device of claim 6, wherein:

the implantable cardiac stimulating device further comprises a high energy shock generator, coupled to the control circuitry, for administering therapeutic shocks through shocking electrodes; and the control circuitry further comprises means for determining the minimum amount of electrical stimulation after a therapeutic shock is administered.

15. The implantable cardiac stimulating device of claim 1, wherein the control circuitry comprises:

means for distinguishing cardiac asystole from ventricular fibrillation.

16. The implantable cardiac stimulating device of claim 15, wherein the means for distinguishing cardiac asystole from ventricular fibrillation comprises:

means for causing the pacing pulse generator to generate a test pacing pulse during a period when the signal representative of cardiac wall motion indicates an occurrence of an undetermined one of cardiac asystole and ventricular fibrillation; and means for monitoring the signal representative of cardiac wall motion for a predetermined period of time following delivery of the test pacing pulse to detect an excursion representing a cardiac contraction, the excursion being indicative of cardiac asystole and an absence of the excursion being indicative of ventricular fibrillation.

17. The implantable cardiac stimulating device of claim 15, further comprising a high energy shock generator, coupled to the control circuitry, for administering a therapeutic shock through shocking electrodes when the control circuitry detects ventricular fibrillation.

18. An implantable system for administering pacing therapy to cardiac tissue in accordance with a patient's capture threshold, the system comprising:

a cardiac wall motion sensor for providing a signal representative of cardiac wall motion;

a pacing pulse generator;

pacing electrodes for delivering pacing pulses generated by the pacing pulse generator to cardiac tissue; and control circuitry for evaluating the signal representative of cardiac wall motion to determine the patient's capture threshold and for causing the pacing pulse generator to generate pacing pulses that provide an amount of electrical stimulation determined in accordance with the patient's capture threshold.

19. The implantable system of claim 18, wherein the signal representative of cardiac wall motion is a cardiac wall acceleration signal.

20. The implantable system of claim 19, wherein the control circuitry comprises:

means for detecting an excursion in the cardiac wall acceleration signal within a predetermined period of time following delivery of a selected pacing pulse, the excursion indicating that the selected pacing pulse provided an amount of electrical stimulation that exceeded the patient's capture threshold.

21. The implantable system of claim 18, wherein the control circuitry comprises:

means for adjusting the amount of electrical stimulation provided by the pacing pulses in response to an indication present in the signal representative of cardiac wall motion that a preceding pacing pulse did not evoke a cardiac contraction.

22. The implantable system of claim 21, wherein the control circuitry further comprises:

means for increasing the amount of electrical stimulation provided by the pacing pulses by a predetermined amount following every pacing pulse that does not evoke a cardiac contraction.

23. The implantable system of claim 18, wherein the control circuitry comprises:

means for determining a minimum amount of electrical stimulation that evokes a cardiac contraction.

24. The implantable system of claim 23, wherein the means for determining a minimum amount of electrical stimulation comprises:

means for decreasing an amount of electrical stimulation provided by the pacing pulses from a sufficient amount of electrical stimulation known to evoke a cardiac contraction until the signal representative of cardiac wall motion indicates a failure of a pacing pulse to evoke a cardiac contraction.

25. The implantable system of claim 24, wherein the means for decreasing the amount of electrical stimulation provided by the pacing pulses comprises:

means for decrementing the amount of electrical stimulation provided by the pacing pulses from the sufficient amount of electrical stimulation by a predetermined amount until the signal representative of cardiac wall motion indicates a failure of a pacing pulse to evoke a cardiac contraction.

26. The implantable system of claim 25, wherein the control circuitry further comprises:

means for resetting the amount of electrical stimulation provided by the pacing pulses to the minimum amount of electrical stimulation that evokes a cardiac contraction after the signal representative of cardiac wall motion indicates a failure of a pacing pulse to evoke a cardiac contraction.

27. The implantable system of claim 26, wherein the control circuitry further comprises:

means for adding a safety margin to the minimum amount of electrical stimulation.

28. The implantable system of claim 24, wherein the control circuitry further comprises:

means for dithering a rate at which the pacing pulses are delivered.

29. The implantable system of claim 23, wherein the control circuitry further comprises:

means for determining the minimum amount of electrical stimulation at predetermined time intervals.

30. The implantable system of claim 23, further comprising a telemetry circuit, coupled to the control circuitry, for receiving an instruction from an external programmer that causes the control circuitry to determine the minimum amount of electrical stimulation.

31. The implantable system of claim 23, wherein:

the implantable system further comprises a high energy shock generator for administering therapeutic shocks through shocking electrodes; and the control circuitry further comprises means for determining the minimum amount of electrical stimulation after a therapeutic shock is administered.

32. The implantable system of claim 18, wherein the control circuitry comprises:

means for distinguishing cardiac asystole from ventricular fibrillation.

33. The implantable system of claim 32, wherein the means for distinguishing cardiac asystole from ventricular fibrillation comprises:

means for causing the pacing pulse generator to generate a test pacing pulse during a period when the signal representative of cardiac wall motion indicates an occurrence of an undetermined one of cardiac asystole and ventricular fibrillation; and means for monitoring the signal representative of cardiac wall motion for a predetermined period of time following delivery of the test pacing pulse to detect an excursion representing a cardiac contraction, the excursion being indicative of cardiac asystole and an absence of the excursion being indicative of ventricular fibrillation.

34. The implantable system of claim 32, further comprising a high energy shock generator, coupled to the control circuitry, for administering a therapeutic shock through shocking electrodes when the control circuitry detects ventricular fibrillation.

35. A method of regulating an amount of electrical stimulation provided by pacing pulses delivered to cardiac tissue from an implantable cardiac stimulating device in accordance with a patient's capture threshold, comprising the steps of:

generating a signal representative of cardiac wall motion;

evaluating the signal representative of cardiac wall to determine the patient's capture threshold; and adjusting the amount of electrical stimulation provided by the pacing pulses in accordance with the patient's capture threshold.

36. The method of claim 35, wherein the generating step comprises the step of generating a cardiac wall acceleration signal.

37. The method of claim 36, wherein the evaluating step comprises the step of:

detecting an excursion in the cardiac wall acceleration signal within a predetermined period of time following delivery of a selected pacing pulse, the excursion indicating that the selected pacing pulse provided an amount of electrical stimulation that exceeded the patient's capture threshold.

38. The method of claim 35, wherein the adjusting step comprises the step of:

increasing the amount of electrical stimulation provided by the pacing pulses by a predetermined amount following every pacing pulse that does not exceed the patient's capture threshold.

39. The method of claim 35, wherein the adjusting step comprises the step of:

decreasing the amount of electrical stimulation provided by the pacing pulses from a sufficient amount of electrical stimulation known to evoke a cardiac contraction until the signal representative of cardiac wall motion indicates a failure of a pacing pulse to evoke a cardiac contraction.

40. The method of claim 39, wherein the decreasing step comprises the step of:

decrementing the amount of electrical stimulation provided by the pacing pulses from the sufficient amount of electrical stimulation by a predetermined amount until the signal representative of cardiac wall motion indicates a failure of a pacing pulse to evoke a cardiac contraction.

41. The method of claim 40, wherein the adjusting step further comprises the step of:

resetting the amount of electrical stimulation provided by the pacing pulses to an amount of electrical stimulation that exceeds the patient's capture threshold after the signal representative of cardiac wall motion indicates a failure of a pacing pulse to evoke a cardiac contraction.

42. The method of claim 41, wherein the adjusting step further comprises the step of:

adding a safety margin to the minimum amount of electrical stimulation.

43. An implantable cardiac stimulating system for distinguishing cardiac asystole from ventricular fibrillation, comprising:

means for generating a signal representative of cardiac wall motion;

means for delivering electrical stimulation to cardiac tissue during a period when the signal representative of cardiac wall motion indicates an undetermined one of cardiac asystole and ventricular fibrillation, the electrical stimulation being sufficient to evoke a cardiac contraction during cardiac asystole; and means for monitoring the signal representative of cardiac wall motion for a predetermined period of time following delivery of the electrical stimulation to detect an excursion representing a cardiac contraction, the excursion being indicative of cardiac asystole and an absence of the excursion being indicative of ventricular fibrillation.

44. The system of claim 43, wherein the means for generating a signal representative of cardiac wall motion comprises an accelerometer.

45. A method of distinguishing cardiac asystole from ventricular fibrillation, comprising the steps of:

generating a signal representative of cardiac wall motion;

delivering electrical stimulation to cardiac tissue during a period when the signal representative of cardiac wall motion indicates an undetermined one of cardiac asystole and ventricular fibrillation, the electrical stimulation being sufficient to evoke a cardiac contraction during cardiac asystole; and monitoring the signal representative of cardiac wall motion for a predetermined period of time following delivery of the electrical stimulation to detect an excursion representing a cardiac contraction, the excursion being indicative of cardiac asystole and an absence of the excursion being indicative of ventricular fibrillation.

46. An implantable cardiac stimulating device for administering pacing pulses to cardiac tissue through an implantable stimulation lead, the device comprising:

a pacing pulse generator for generating the pacing pulses;

a cardiac wall acceleration sensor for producing a cardiac wall acceleration signal corresponding to a mechanical cardiac contraction;

detecting means for detecting the absence of a cardiac wall acceleration signal corresponding to loss of capture;

control circuitry, coupled to the pacing pulse generator and the detecting means, for controlling the pacing pulse generator and for automatically increasing an amount of electrical stimulation energy provided by the pacing pulses whenever the cardiac wall acceleration signal indicates loss of capture.

47. The implantable cardiac stimulating device of claim 46, wherein the control circuitry further comprises:

means for automatically detecting capture threshold.

48. The implantable cardiac stimulating device of claim 47, wherein the control circuitry further comprises:

means for automatically adjusting the amount of electrical stimulation provided by the pacing pulses to a safety margin above the detected capture threshold.

* * * * *